United States Patent [19]

Shasha et al.

[11] 4,277,364

[45] Jul. 7, 1981

[54] ENCAPSULATION BY ENTRAPMENT

[75] Inventors: Baruch S. Shasha, Peoria; William M. Doane, Morton; Charles R. Russell, Peoria, all of Ill.

[73] Assignee: The United States of America as represented by the Secretary of Agriculture, Washington, D.C.

[21] Appl. No.: 733,968

[22] Filed: Oct. 19, 1976

Related U.S. Application Data

[63] Continuation-in-part of Ser. No. 642,836, Dec. 22, 1975, abandoned.

[51] Int. Cl.$^3$ .................. B01J 13/02; A01N 25/26
[52] U.S. Cl. .......................................... 252/316; 71/3; 71/64 F; 71/66; 71/100; 71/117; 424/19; 424/22; 424/35; 424/213; 424/354; 427/214
[58] Field of Search .................. 252/316; 424/19, 35, 424/22; 71/64 F, 66, 100, DIG. 1; 427/214

[56] References Cited

U.S. PATENT DOCUMENTS

| | | | |
|---|---|---|---|
| 3,160,552 | 12/1964 | Russell et al. | 536/103 X |
| 3,247,066 | 4/1966 | Milosovich, Jr. | 424/37 X |
| 3,576,660 | 4/1971 | Bayless et al. | 252/316 X |
| 3,576,760 | 4/1971 | Gould et al. | 424/32 X |
| 3,669,722 | 6/1972 | Bishop | 428/402 |
| 3,778,383 | 12/1973 | Schibler et al. | 252/316 |

FOREIGN PATENT DOCUMENTS 1163023  9/1969  United Kingdom ..................... 252/316

OTHER PUBLICATIONS

R. E. Grim: Clay Mineralogy, 2nd Ed., (1968), pp. 185–186, 212, 213.
E. G. Hallsworth: 3rd International Symposium on Soil Conditioning, (1975), pp. 3–11.

*Primary Examiner*—Richard D. Lovering
*Attorney, Agent, or Firm*—M. Howard Silverstein; David G. McConnell; Curtis P. Ribando

[57] ABSTRACT

Water-soluble and water-insoluble solid and liquid core materials are encapsulated by the same method. Core materials are simply entrapped in a matrix of water-insoluble polyhydroxy polymers which are insolubilized from their corresponding water-soluble xanthates in the presence of the core materials. Encapsulation of biologically active compositions provides a shield against hostile environments, improves safety in handling, and slows the release of such compounds to the surrounding medium. Highly volatile liquids are protected against losses by evaporation. Encapsulation also provides protection against decomposition from exposure to ultraviolet light.

30 Claims, No Drawings

ENCAPSULATION BY ENTRAPMENT

CROSS-REFERENCES TO RELATED APPLICATIONS

This is a continuation-in-part of Ser. No. 642,836 filed Dec. 22, 1975, now abandoned.

BACKGROUND OF THE INVENTION

1. Field of the Invention

The invention relates to a method of encapsulating materials by entrapment in a matrix of water-insoluble polyhydroxy polymers and to the compositions prepared thereby.

2. Description of the Prior Art

Prior art methods of encapsulation can be described in two major categories, physicomechanical and chemical. Physicomechanical techniques include the following:

a. Spray drying: An emulsion is prepared with a film-forming polymer dissolved in the continuous phase. The emulsion is then dried by spraying into a stream of hot inert gas. Before spray drying the wall materials can be strengthened by crosslinking the polymer wall material. See U.S. Pat. Nos. 3,016,308 and 3,429,827.

b. Dipping or centrifuging technique: Core material particles or droplets are passed through a thin film of liquid wall-forming material. The wall material is then hardened. See U.S. Pat. No. 3,015,128.

c. Multiple nozzle spraying: Core material is sprayed from an inner orifice while the wall material is sprayed from a concentric ring orifice. In this manner water or aqueous solutions are encapsulated in paraffin or other waxes. See U.S. Pat. No. 3,423,489.

d. Fluidized bed coating: Particles are held suspended by a vertical stream of air and sprayed with wall material which, after evaporation of solvent, forms a solid film around the core material. This technique is used when solid particles are to be encapsulated.

e. Electrostatic microencapsulation: Atomized core material and molten wall material are oppositely charged and mixed in a collision chamber. The thusly encapsulated particles are held in suspension and cooled to form the powdered product. See U.S. Pat. No. 3,159,874.

f. Vacuum encapsulation: Wall material is volatilized in a vacuum and deposited on colder nonvolatile core material particles which are in a rotary motion.

The most important chemical encapsulation techniques include the following:

a. Coacervation: The attraction between colloids and water of solvation is altered to such an extent that the colloid particles will tend to aggregate to form two separate and distinct liquid phases within the colloidal suspension. Both phases contain the same components with one phase (the coacervate) having a much greater concentration of colloid than the other.

The encapsulation occurs when small droplets of oil (a completely water-immiscible liquid) are present in the colloidal suspension. As the coacervate is formed it is deposited around individual droplets. The coacervate must then be hardened (gelled) by lowering the temperature below the gel point. The capsules are then dehydrated and permanently hardened.

(1) Simple coacervation: A single colloid is dispersed in water and the water of solvation is removed from around the colloid by addition of chemical compounds which have a greater affinity for water than the colloid (e.g., salts or alcohols). This causes the colloid chains to come closer together and form the coacervate.

(2) Complex coacervation: Ionic charges on the colloid chains are neutralized by mixing two colloids carrying opposite charges. See U.S. Pat. Nos. 2,800,458 and 2,800,457.

b. Interfacial polymerization: This method necessitates the use of at least a two-phase system. One of the reactants must be soluble in the continuous phase and insoluble in the discontinuous phase (core material). The other reactant must be insoluble in the continuous phase and soluble in the discontinuous phase. The polymerization reaction occurs at the interface between the two phases forming a polymer shell around the core material, thereby completely enveloping it. This shell must be insoluble in both phases. In this method either phase can be an aqueous system. See U.S. Pat. Nos. 3,577,515 and 3,575,882 and British Pat. No. 1,163,023.

For additional information and references see "Microencapsulation, Processes and Application", J. E. Vandegaer, ed., Plenum Press, New York and London, 1974, pp. 1–37 and 89–94; W. Sliwka, Agnew. Chem., Internat. Edit., Vol. 14, No. 8, pp. 539–550, 1975; and "Capsule Technology and Microencapsulation", M. Gutcho, ed., Noyes Data Corporation, Park Ridge, N.J., 1972.

The above encapsulation methods are multistep processes which require carefully controlled conditions or special equipment. They are time consuming and expensive, often requiring elevated temperatures and pressures other than ambient; and they all require at least a two-phase system. Many require expensive, toxic, and flammable solvents which must be recovered. Coacervation is limited to the encapsulation of oils in materials which have the capacity to form gels. Interfacial polymerization techniques, also requiring two or more phases, are limited essentially to expensive synthetic polymerization systems, many of which are petrochemicals and which generally produce nonbiodegradable polymers. To make these systems more economical and to prevent ecological contamination, unreacted monomers must be recovered. The only system that appears to be useful for coating solid particles is the fluidized bed technique.

SUMMARY OF THE INVENTION

In contrast to prior art encapsulation systems, the chemical encapsulation method that we have discovered has the advantage of operating not only in aqueous and nonaqueous two-phase systems, but also in single-phase systems in which a matrix-forming material and core material are soluble in the same solvent. The encapsulation system is also operative for water-insoluble liquids and solid particulate core material dispersed in the aqueous solution of matrix-forming material. The method of the invention uses neither the coacervation nor the interfacial polymerization techniques but is a method of encapsulating a substance by quickly insolubilizing a polyhydroxy polymer xanthate in the presence of suitable core material which is thereby entrapped within the insolubilized matrix. The method operates at ambient temperatures and pressures.

The method comprises the following steps:

a. preparing a dispersion or solution of a suitable chemical biological agent in a first matrix-forming material comprising an aqueous solution of a polyhydroxy polymer xanthate (PPX) having a xanthate degree of substitution of from about 0.1 to 3, wherein the relative amount of said PPX with respect to said biological agent is sufficient to entrap said agent within a matrix of said PPX;

b. reacting the PPX with a coupling agent at a pH of from about 2 to about 7 to form a first insolubilized matrix thereby entrapping said agent;

b'. optionally redispersing said first matrix from step (b) in a second matrix-forming material comprising an aqueous solution of PPX;

b''. reacting the PPX in step (b') with a coupling agent at a pH of from about 2 to about 7 to form a second insolubilized matrix thereby further entrapping said agent; and c. recovering said entrapped chemical biological agent.

The product is a composition of matter comprising: (1) a matrix of a polyhydroxy polymer disulfurdicarbothionate, a polyvalent metal dithiocarbonate of a polyhydroxy polymer, or an alkyl dithiocarbonate of a polyhydroxy polymer; and (2) an effective amount of a suitable chemical biological agent (i.e., core material) encapsulated within the matrix.

In an alternate embodiment, a synthetic polymer or a rubber latex can be included in the first and/or second matrix-forming material in order to impart certain desired properties to the matrix, such as modified release characteristics.

The method of the invention has the further advantage of encapsulating both volatile and nonvolatile core materials. Core materials can be either liquid or finely divided solids, organic or inorganic, polar or nonpolar. If a two-phase system is used, it is not necessary to form an emulsion. Simple hand mixing of the components is sufficient.

It is an object of the invention that the encapsulating materials be generally less expensive than those used in the prior art and be inclusive of those derived from natural, renewable resources.

It is also an object of the invention to sufficiently entrap biologically active chemicals in a matrix to increase the safety in handling them, to slow their release to the environment, and to reduce losses due to volatility and decomposition by sunlight.

DETAILED DESCRIPTION OF THE INVENTION

Polyhydroxy polymer xanthates (PPX) suitable for use in accordance with the invention are prepared from any natural or synthetic polyhydroxy polymer capable of forming xanthate derivatives of suitable xanthate degree of substitution (D.S.) including starches, starch fractions (e.g., amylose and amylopectin), methyl starch, hydroxyethyl starch, cereal flours (e.g., from whole wheat, bran, refined wheat, and wheat fractions), depolymerized flours, cellulose, methyl cellulose, hydroxyethyl cellulose, dextrin, dextran, guar gum, biopolymers (e.g., xanthan gum), cationic starch, anionic starch, and synthetic poly alcohols (e.g., polyvinyl alcohol). Suitable xanthate D.S.'s fall within the range of from 0.1 to 3, preferably from 0.1 to 1. The PPX is employed as an aqueous system, wherein the operable range of PPX concentration for effective matrix formation is from about 5% to about 70%, with a range of 10% to 50% being preferred.

The reaction by which the PPX is insolubilized to form the matrix around the core materials is fully described in commonly assigned U.S. Pat. No. 3,160,552 and by Russell et al., Tappi 45(7): 557–566 (July 1962) which are herein incorporated by reference. Heretofore the reaction of certain PPX compositions with coupling compounds, as described in the above references, has been essentially confined to the preparation of paper having increased wet and dry strengths, to paper coatings, and to reinforced rubbers (U.S. Pat. No. 3,830,762). Suitable coupling agents are contained in three basic categories: oxidative coupling agents which include sodium nitrite, nitrous acid, iodine, chlorine, sodium tetrathionate, cyanogen bromide, nitrosyl chloride, chloramine T, and hydrogen peroxides; polyvalent metal ion coupling agents which include water-soluble salts of $Hg^{+2}$, $Fe^{+2}$, $Fe^{+3}$, $Zn^{+2}$, $Cu^{+2}$, $Cd^{+2}$, $Pb^{+2}$, $Mn^{+2}$, $Ni^{+2}$, and $Cr^{+3}$; and difunctional coupling agents such as alkyl dihalides, diepoxides, and epihalohydrins. Examples of the dihalides are dibromomethane, dibromopropane, and dichlorobutane. Examples of the diepoxides are 1,2:3,4-diepoxybutane, 1,2:4,5-diepoxypentane, and 1,2:7,8-diepoxyoctane. Examples of the epihalohydrins are epichlorohydrin and epibromohydrin. The basic matrix structures resulting from each of the above categories of coupling agents are depicted below:

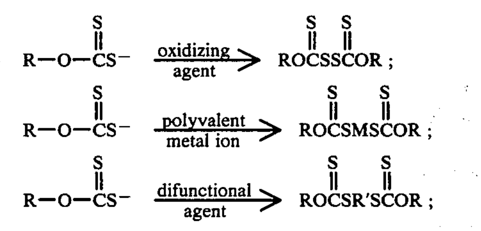

(1)
(2)
(3)

where M=polyvalent metal ion; R=polyhydroxy polymer; and R'=alkyl or substituted alkyl.

It is to be understood that the alkyl or substituted alkyl in structure (3) above is derived from the specific difunctional coupling agent employed. Other coupling agents which will be considered suitable for use in accordance with the invention will be known to those skilled in the art.

Reactions of PPX with coupling agents to form an insolubilized matrix usually require a pH of from about 2 to about 7, though a pH of from 4 to 7 is preferred.

The order of addition of coupling agent and pH adjustment is not critical for most coupling agents. However, when sodium nitrite is used, it is preferable to adjust the pH of the reaction medium after the coupling agent has been added, and with hydrogen peroxide it is preferable to adjust the pH first. The resulting matrix may then be washed, filtered, and dried by any conventional method. The matrix washing can be with water or any other solvent that does not dissolve or react with the matrix material without loss of core material. However, after the matrix has been dried to yield a friable granular or powdered material, rewetting initiates biodegradation of the matrix material and release of the core material begins.

The usual reaction parameters of the above reaction (i.e., ambient temperature, pressure, etc.) are all well known to those skilled in the art and will not be considered herein.

Core materials to be encapsulated and suitable for use in accordance with the invention include any organic and inorganic solid capable of being finely divided or liquid that is water soluble, water insoluble, or water dispersible that does not interfere with the encapsulating process and does not react with or dissolve the encapsulating matrix.

Suitable chemical-biological agents are defined herein as including essentially all known herbicides, insecticides, fungicides, nematocides, bacteriocides, rodenticides, moluscides, acaricides, larvacides, animal, insect, and bird repellents, plant growth regulators, fertilizers, pheromones, sex lures and attractants, and flavor and odor compositions. Suitable examples of herbicides include S-propyl dipropylthiocarbamate, $\alpha,\alpha,\alpha$-trifluoro-2,6-dinitro-N,N-dipropyl-p-toluidine, S-ethyl diisobutylthiocarbamate, 2,6-dichlorobenzonitrile, 1,1'-dimethyl-4,4'-bipyridinium dichloride, 2,4-dichlorophenoxy acetic acid, sodium 2,4-dichlorophenoxy acetate, and ammonium 3-amino-2,5-dichlorobenzoate. Suitable examples of nematocides include 1,2-dibromo-3-chloropropane. Suitable examples of suitable insecticides include O-ethyl-S-phenylethyl phosphorodithioate, S-(1,2-dicarbethoxyethyl)-O,O-dimethyl dithiophosphate, methyl O,O-dimethyl-o,p-nitrophenyl phosphorothioate, 1,1,1-trichloro-2,2-bis(p-chlorophenyl), and 2,3-dihydro-2,2-dimethyl-7-benzofuranyl methyl carbamate. Suitable sex lures or attractants include methyl 4-allyl-2-methoxyphenol and tertiarybutyl 4-chloro-2-methyl cyclohexane carboxylate. For comprehensive lists of suitable pesticide compositions see O. Johnson, Chemical Week, pp. 39–64, June 21, 1972. Other compositions suitable as core materials for use in accordance with the invention will be known to those skilled in the art. Core materials dissolved in water-immiscible solvents and compatible combinations of the above types of compositions are also easily encapsulated by the instant method.

Effective amounts of core materials depend entirely on the type and characteristics of the core material, on matrix thickness, and on intended utility of the product. A very volatile liquid would require a thicker or a more impermeable matrix structure than a nonvolatile solid. A volatile liquid to be used as a slow-release pesticide, for example, would require less matrix material than a volatile liquid to be completely withheld from the environment. In the latter instance a subsequent coating with an impermeable polymer, such as those disclosed in the prior art, could be applied to the instant product as discussed below. Matrix thickness is also controlled by a second coating of PPX. This is accomplished by resuspending the first insolubilized encapsulated product in a solution of PPX, adding the coupling agent, and adjusting pH to from about 2 to about 7 to form a second matrix in the same manner as the first matrix. Additional coatings are applied in the same manner to build up the desired matrix thickness.

Release characteristics of matrix materials may also be altered by treating the instant product with a combination of resorcinol and formaldehyde, or other hardening agents as well known in the art. The hardening agents may be added to the matrix material before, during, or after insolubilization. Not only is the release of core materials from the instant product slowed on treatment with resorcinol and formaldehyde, but also this treatment facilitates dewatering and filtration of the instant product. The effective range of hardening agent concentration is from about 0.1% to about 10%, based on the dry weight of the PPX, with a range of 2% to 5% being preferred.

Release characteristics may also be modified by combining PPX with other materials such as rubber latexes. Without limitation thereto, examples of rubber latexes useful for combining with PPX include styrene-butadiene (SBR), styrene-acrylonitrile-butadiene, acrylonitrile-butadiene, isoprene, isoprene-acrylonitrile, isoprene-butadiene, and chloroprene (neoprene). PPX-latex combinations have been found to be effective as matrix-forming materials in first encapsulations as well as subsequent encapsulations. Rubber latexes can also be used alone as coating materials for the PPX matrix. The preferred range of ratios of rubber latex:total amount of PPX is from about 4:1 to about 1:9 by dry weight. Further modification of release properties of the PPX-rubber latex combinations may be achieved by incorporating effective amounts of rubber curing agents and curing accelerator agents, such as sulfur, carbon disulfide, butyl 8, and others as known in the art. Addition of such agents to the material mixture prior to matrix insolubilization is preferred.

In still another embodiment, the release characteristics of matrix materials may be altered by adding to the solution of PPX a synthetic polymer dissolved in an organic solvent. Most synthetic polymers are operable for this purpose, particularly the polyvinyl and polyacrylic types. Without desiring to be limited to any particular species, examples of suitable polymers are polystyrene, polyethylene, poly(vinyl chloride), and poly(methyl methacrylate). The polymer is dissolved in any suitable organic solvent as known in the art, such as benzene or toluene. Such PPX-organic soluble synthetic polymer combinations can be used as matrix-forming materials in first and/or subsequent encapsulations. The amount of synthetic polymer can range from 0–30%, dry weight basis, of the matrix combination, the preferred range being 1–25%. Alternatively, the organic soluble synthetic polymers can be used alone as a coating for the PPX matrix. The rubber latexes discussed above can also be incorporated to yield matrix-forming materials comprising PPX-organic soluble synthetic polymer-rubber latex combinations.

An effective amount of a suitable biological agent is defined herein as that amount of core material which will achieve the desired result (e.g., attract, repel, or kill pests, give off a detectable aroma or flavor, or enhance the growth of plants) when the encapsulated composition containing the effective amount of the suitable biological agent is placed in the proper environment. For purposes of sufficient entrapment within the matrix, it is preferred that the suitable chemical biological agent is present in the matrix-forming material before the encapsulating reaction in an amount equal to from about 1% to about 100% of the total amount of matrix-forming material on a dry weight basis. The resulting composition of matter, therefore, preferably contains a biological agent in amounts of from 1% to 50% of the total weight of the composition of matter on a dry weight basis.

The release of the biological agent requires that the environment in which the encapsulated composition is placed contains moisture. Fields, gardens, and the like in which pesticides, attractants, repellents, plant growth regulators, and fertilizers are normally used contain sufficient natural or added moisture to cause the release of the chemical biological agent. Odor and flavor compositions, which are used in foods, are released from the encapsulating matrix by moisture contained in or added to the food product. While not desiring to be bound to any particular theory, it is believed that the mechanism of release is effected by the biodegradation of the PPX matrix as well as by displacement by water and diffusion through imperfections in the matrix.

The following examples are intended to further illustrate the invention and should not be construed as limiting the invention which is defined by the claims. All parts and percentages herein are by weight unless otherwise specified.

EXAMPLE 1 a. Starch, 162 parts, was suspended in 1000 parts of water. Carbon disulfide, 36 parts, and 40 parts sodium hydroxide in 345 parts water were added to the starch suspension. The suspension was stirred and allowed to stand for 30 minutes at 25° C. to yield a starch xanthate (D.S. 0.35) solution having a concentration of 13.7%.

b. The procedure described in (a) above was repeated with 324 parts of starch in 2600 parts of water, 24.3 parts of carbon disulfide, and 40 parts of NaOH in 345 parts of water. The reaction mixture was allowed to stand for 1 hour at 25° C. to yield a starch xanthate (D.S. 0.1) having a concentration of 12.9.

c. The procedure described in (a) above was repeated with 32 parts of starch in 150 parts water, 25 parts carbon disulfide, and 32 parts NaOH in 110 parts water. The reaction mixture was allowed to stand for 1 hour at 25° C. to yield a starch xanthate (D.S. 1.0) having a concentration of 16%.

d. The procedure described in (a) above was repeated with 32.4 parts of starch in 100 parts water, 2.4 parts carbon disulfide, and 4 parts NaOH in 56 parts water. The reaction mixture was allowed to stand 1 hour at 25° C. to yield a starch xanthate (D.S. 0.1) solution having a concentration of 21.2%.

e. One hundred eighty parts of acid modified corn flour—90 fluidity—were mixed with 180 parts of water followed by 20 parts of carbon disulfide and 40 parts of 50% sodium hydroxide to yield the corresponding xanthate flour (D.S. 0.17) having a concentration of 47%.

f. One hundred eighty parts of acid modified starch—90 fluidity—were suspended in 250 parts of water followed by treatment with 40 parts of carbon disulfide and 80 parts of 50% sodium hydroxide solution to yield the corresponding xanthate (D.S. 0.35) having a concentration of 44%.

g. Three hundred sixty parts of acid modified starch—90 fluidity—were mixed with 300 parts of water followed by 20 parts of carbon disulfide and 40 parts of 50% sodium hydroxide solution to yield the corresponding xanthate (D.S. 0.07) having a concentration of 53%.

EXAMPLE 2

One part cellulose powder was mixed with 10 parts of an 18% aqueous solution of NaOH and 5 parts carbon disulfide. The reaction mixture was kept at about 25° C. for 4 hours with occasional stirring. The resulting rubbery mass was diluted with 30 parts water and mixed thoroughly with 1 part of the herbicide S-propyl dipropylthiocarbamate (6.9% nitrogen), and 1 part $NaNO_2$. The pH of the mixture was adjusted to 4.5 with 25% aqueous acetic acid. The resulting yellow cake was washed with water and dried at about 25° C. to yield 1.7 parts of a yellow granular material having a sulfur content of 15.5% and a nitrogen content of 1.1%. The product contained 16% encapsulated core material.

EXAMPLE 3

Sixty-six parts of starch xanthate solution from Example 1(a) were mixed with 4 parts of the herbicide S-propyl dipropylthiocarbamate (6.9% nitrogen), and 3 parts $NaNO_2$. A 10% aqueous solution of acetic acid was added with mixing until the pH of the reaction mixture was 4.2. After standing for 10 minutes at about 25° C. the resulting matrix was filtered, washed with water, and dried at about 25° C. to yield 11.7 parts of product having 2.06% nitrogen. The product contained 30% encapsulated core material. After standing for 40 days at 25° C. in an open container, the product contained 28.7% encapsulated core material.

Although the S-propyl dipropylthiocarbamate core material is very soluble in acetone-hexane mixtures and in acetone alone, these solvents were unable to extract substantial amounts of core material from the encapsulated product. Two parts of the encapsulated product were allowed to stand in 25 parts of an equal volume mixture of hexane and acetone for 5 minutes. The solvent was drained off and the product was allowed to stand in 25 parts acetone for an additional 5 minutes. Nitrogen analysis on the subsequently dried product gave a value of 1.64% (i.e., 23.8% core material). Encapsulation also provides a shield against evaporation losses. Free core material (0.206 part) was placed in an evaporating dish while 0.800 part of the encapsulated product was placed on a second evaporating dish. Both dishes were subjected to the same conditions of temperature and simulated sunlight. After 25 hours there was 100% loss of the free core material, while the nitrogen value of the encapsulated material decreased only from 2.06% to 1.85%, a decrease in the percent of core material of from 30% to 26.8%.

Germination studies, using the above encapsulated product, were performed in 12 containers each containing 50 g. top soil. Eight of the containers (No. 5–12) were treated with 30 mg. of the encapsulated herbicide. On the first day containers 1–4 containing no encapsulated herbicide and containers 5–8 were each planted with 100 grass seeds. On the third day (grass seeds in containers 1–4 had germinated), containers 9–12 were each planted with 100 grass seeds. Each container was watered with 20 ml. of water when the seeds were planted and every 48 hours thereafter. On the tenth day there was no germination in containers 5–8, the grass in containers 9–12 was about 1 inch tall, and the grass in containers 1–4 was about 7 to 8 inches tall.

EXAMPLE 4

The encapsulation process described in Example 3 was repeated with 104 parts of starch xanthate solution of Example 1(a), 3 parts $NaNO_2$, and 5 parts of the herbicide α,α,α-trifluoro-2,6-dinitro-N,N-dipropyl-p-toluidine in 10 parts acetone to yield 21 parts of encapsulated product containing 23.8% core material.

EXAMPLE 5

The encapsulation process described in Example 3 was repeated with 51 parts of starch xanthate solution of Example 1(a), 1.5 parts $NaNO_2$, and 1.5 parts of the herbicide α,α,α-trifluoro-2,6-dinitro-N,N-dipropyl-p-toluidine in 5 parts acetone to yield 14.5 parts of encapsulated product containing 35.6% core material (i.e., 5.17% nitrogen).

Four containers were filled with 50 g. of top soil and 10 mg. of the above encapsulated product, and four containers were filled with only 50 g. of top soil. One hundred grass seeds were distributed on top of the soil in each container which was then watered with 20 ml. of water every 48 hours. After 1 week 60–100% of the seeds had germinated in the containers containing no herbicide, while no germination occurred in those containing herbicide.

EXAMPLE 6

The encapsulation process described in Example 3 was repeated with 100 parts of starch xanthate solution of Example 1(a), 3 parts $NaNO_2$, and 5 parts of the herbicide S-ethyl diisobutylthiocarbamate to yield 20.3 parts of encapsulated product containing 23.6% core material (i.e., 1.52% nitrogen).

EXAMPLE 7

Forty-one parts of starch xanthate solution of Example 1(c) were mixed with 100 parts of water and 3.1 parts of the herbicide S-ethyl diisobutylthiocarbamate followed by the addition of 5 parts of glacial acetic acid and 4 parts of 20% aqueous hydrogen peroxide. After continuation of mixing for 10 minutes the resulting matrix was filtered, washed with water, refiltered, and dried at about 25° C. to yield 11 parts of encapsulated product containing 1.71% nitrogen and 26.6% core material.

EXAMPLE 8

The encapsulation process described in Example 7 was repeated with 45 parts of starch xanthate solution of Example 1(a), 2 parts glacial acetic acid, 2 parts $H_2O_2$, and 4.1 parts of the herbicide S-ethyl diisobutylthiocarbamate to yield a wet cake which was mixed with 10 parts clay. The dried mixture contained 36 parts of product containing 3.8% core material.

EXAMPLE 9

The starch xanthate solution of Example 1(a) (40.5 parts) was mixed with 5 parts of the herbicide S-ethyl diisobutylthiocarbamate and 10 parts 25% aqueous acetic acids. Upon the addition with stirring of 1 part of 30% aqueous hydrogen peroxide, an insoluble matrix formed. The mixing was continued for 10 minutes, followed by the addition of 13 parts starch xanthate solution of Example 1(a), 3 parts 25% aqueous acetic acid, and 0.5 part 30% aqueous hydrogen peroxide. The resulting doubly encased product was filtered, washed with water, refiltered, and dried at room temperature (i.e., about 25° C.) to yield a light yellow powder having a nitrogen value of 2.42% and containing 37.5% core material.

EXAMPLE 10

Twenty-six parts of starch xanthate solution of Example 1(a) were mixed with 2.5 parts of the herbicide S-ethyl diisobutylcarbamate, and 1 part of $NaNO_2$. Aqueous acetic acid (25) was added dropwise to produce a thick gel to which was added 1 part glacial acetic acid. The mixture containing the resulting matrix was filtered, washed with water, and refiltered. The product was added to 5 parts starch xanthate solution [Example 1(a)] and 13 parts of SBR 1502 latex[a] (20% solids). The mixture was acidified with acetic acid, filtered, washed with water, refiltered, and dried at about 25° C. to yield 7.5 parts of a double encapsulated product containing 2.04% nitrogen and 31.6% core matrial.

[a] SBR 1502 latex is a commercial rubber latex containing 20% solids in water. The rubbers comprise 23.5% styrene and 76.5% butadiene. The emulsifier is a mixture of fatty acid and rosin acid.

EXAMPLE 11

The encapsulation process described in Example 9 was repeated with 39 parts of starch xanthate solution of Example 1(a), 8 parts 25% aqueous acetic acid, 1 part 30% aqueous $H_2O_2$, and 3.9 parts of the herbicide S-ethyl diisobutylthiocarbamate for the first encapsulation, and 5 parts of starch xanthate solution of Example 1(a), 2 parts 25% aqueous acetic acid, and 0.5 part 30% aqueous $H_2O_2$ to yield 16.7 parts of a double encapsulated product containing 1.28% nitrogen and 19.7% core material. Drying was accomplished by cycling the product five times at 65° C. through a flash drier.

EXAMPLE 12

The encapsulation process described in Example 9 was repeated with 20 parts of starch xanthate solution of Example 1(a), 1.5 parts $ZnSO_4.7H_2O$, 5 parts 25% aqueous acetic acid, and 1.2 parts of the herbicide S-ethyl diisobutylthiocarbamate for the first encapsulation, and 6 parts of starch xanthate solution of Example 1(a), 2 parts 25% aqueous acetic acid, and 0.5 part 30% aqueous $H_2O_2$ to yield 5.2 parts of a double encapsulated product containing 1.33% nitrogen and 20.6% core material.

EXAMPLE 13

The encapsulation process described in Example 3 was repeated with 25 parts of starch xanthate solution of Example 1(c), 0.6 part $NaNO_2$, and 1.9 parts of the herbicide S-ethyl diisobutylthiocarbamate contained in 4 parts SBR 1502 latex (20% solids), and one drop Tween 85 emulsifier to yield 8.2 parts of encapsulated product containing 1.5% nitrogen and 23.2% core material.

One gram of the encapsulated product lost only 16% core material through evaporation by standing for 20 hours at 25° C. in an open container, while under the same conditions free core material completely evaporated.

EXAMPLE 14

The encapsulation process described in Example 10 was repeated with 20 parts of starch xanthate solution of Example 1(a), 1 part $NaNO_2$, and 2.5 parts of the herbicide S-ethyl diisobutylthiocarbamate for the first encapsulation, and 3 parts SBR 1502 latex (20% solids) and 1 part glacial acetic acid to yield 6 parts of a double encapsulated product containing 2.2% nitrogen and 34% core material.

EXAMPLE 15

The encapsulation process described in Example 10 was repeated with 40 parts of starch xanthate solution of Example 1(a), 2 parts $NaNO_2$, 4 parts glacial acetic acid, and 6 parts of the nematocide 1,2-dibromo-3-chloropropane for the first encapsulation, and 12 parts of starch xanthate solution of Example 1(a) and 1 part glacial acetic acid to yield 16 parts of a double encapsulated product containing 18% halogen and 21.7% core material. The double encapsulated product gave off a strong odor typical of 1,2-dibromo-3-chloropropane after standing in water for 15 minutes.

EXAMPLE 16

The encapsulation process described in Example 10 was repeated with 28 parts of starch xanthate solution of Example 1(a), 1 part $NaNO_2$, and 5 parts of the nematocide 1,2-dibromo-3-chloropropane for the first encapsulation, and 5 parts of starch xanthate solution of Example 1(a), 0.5 part glacial acetic acid, and 1 part 20% aqueous $H_2O_2$ to yield 22.5 parts of a double encapsulated product containing 18.5% halogen and 22.2% core material. The double encapsulated product gave off a strong odor typical of 1,2-dibromo-3-chlorpropane after standing in water for 15 minutes.

EXAMPLE 17

The encapsulation process described in Example 3 was repeated with 50 parts of starch xanthate solution of Example 1(a), 2 parts $NaNO_2$, and 7.5 parts of the 1,2-dibromo-3-chloropropane to yield 8 parts of encapsulated product containing 14.4% halogen and 17.4% core material. The amount of core material remained unchanged after standing in an open container for 4 months at 5° C. The encapsulated product gave off a strong odor typical of 1,2-dibromo-3-chloropropane after standing in water for 15 minutes.

EXAMPLE 18

The encapsulation process described in Example 9 was repeated with 30.7 parts of starch xanthate solution of Example 1(a), 8 parts 25% aqueous acid, 2 parts 20% aqueous $H_2O_2$, and 3.5 parts of the insecticide O-ethyl-S-phenylethyl phosphorodithioate for the first encapsulation, and 8 parts of starch xanthate solution of Example 1(a), 2 parts 25% aqueous acetic acid, and 1 part 20% aqueous $H_2O_2$ to yield 10 parts of a double encapsulated product containing 30.6% core material.

EXAMPLE 19

The encapsulation process described in Example 3 was repeated with 100 parts of starch xanthate solution of Example 1(a), 3 parts $NaNO_2$, and 10 parts of the insecticide S-(1,2-dicarbethoxyethyl)-O,O-dimethyl dithiophosphate to yield 23 parts of encapsulated product containing 39% core material.

EXAMPLE 20

The encapsulation process described in Example 3 was repeated with 150 parts of starch xanthate solution of Example 1(a), 5 parts $NaNO_2$, and 5 parts of the herbicide 2,6-dichlorobenzonitrile to yield 3 parts of encapsulated product containing 7.2% chlorine and 16.6% core material. There was no loss in chlorine content after standing in an open container at 25° C. for 5 months.

EXAMPLE 21

The encapsulation process described in Example 3 was repeated with 60 parts of starch xanthate solution of Example 1(a), 1.5 parts $NaNO_2$, and 6 parts of a mixture of 80% of the insecticide methyl O,O-diethyl-o,p-nitrophenyl phosphorothioate and 20% xylene to yield 12.2 parts of encapsulated product containing 2.48% phosphorus and 24.2% core material. A sample of the above encapsulated product was allowed to stand in water. Aliquots were periodically withdrawn for 2 hours and tested for ultraviolet absorption maximum at 276 nm, the absorption region for the above core material. Absorption was observed in all aliquots indicating that core material was being released.

EXAMPLE 22

The encapsulation process described in Example 9 was repeated with 52 parts of starch xanthate solution of Example 1(a), 2.5 parts glacial acetic acid, 2 parts 20% aqueous $H_2O_2$, and 6 parts of a mixture of 80% of the insecticide methyl 0,0-diethyl-o,p-nitrophenyl phosphorothioate and 20% xylene for the first encapsulation, and 8 parts of starch xanthate solution of Example 1(a), and 0.5 part glacial acetic acid to yield 13 parts of a double encapsulated product containing 2.84% phosphorus and 27.6% core material.

EXAMPLE 23

The encapsulation process described in Example 3 was repeated with 62 parts of starch xanthate solution of Example 1(a), 1.5 parts $NaNO_2$, and 5 ml. aqueous solution containing 29.1% of the aquatic herbicide 1,1'-dimethyl-4,4'-bipyridinium dichloride to yield 9.5 parts of encapsulated product containing 0.45% nitrogen and 3.0% core material.

EXAMPLE 24

Twenty parts of the herbicide 2,4-dichlorophenoxy acetic acid (2,4-D) was dissolved in 150 parts of absolute ethanol and 18% aqueous sodium hydroxide was added to a pH of about 9. The resulting precipitate (i.e., the sodium salt of 2,4-D) was washed with absolute ethanol and dried.

The encapsulation process described in Example 7 was repeated with 80 parts of starch xanthate solution of Example 1(a), 6 parts 25% aqueous acetic acid (pH of reaction mixture was 5.5), 6 parts of 20% aqueous $H_2O_2$, and 8 parts of the sodium salt of 2,4-D to yield 20 parts of encapsulated product containing 12.7% chlorine and 39.2% core material.

The encapsulated product is odorless in contrast to the free 2,4-D sodium salt or 2,4D (both have a sharp phenolic odor). In contrast to free 2,4-D or 2,4-D sodium salt, the encapsulated product is stained dark blue when contacted with an aqueous iodine solution.

EXAMPLE 25

The encapsulation process described in Example 7 was repeated with 52 parts of starch xanthate solution of Example 1(a), 2 parts glacial acetic acid, 2 parts 20% aqueous $H_2O_2$, and 3.2 parts of the herbicide ammonium 3-amino-2,5-dichlorobenzoate, 90% purity, to yield 9 parts of encapsulated product containing 8% chlorine and 22.8% core material.

EXAMPLE 26

The encapsulation process described in Example 3 was repeated with 47 parts of starch xanthate solution of Example 1(a), 1 parts $NaNO_2$, and 3 parts of the insecticide 1,1,1-trichloro-2,2-bis(p-chlorophenyl)ethane (i.e., DDT) in 6 parts acetone to yield 9.8 parts of encapsulated product containing 15.4% chlorine and 30.8% core material.

EXAMPLE 27

The encapsulation process described in Example 3 was repeated with 40 parts of starch xanthate solution of Example 1(b), 1 part NaNO$_2$, and 3 parts of the insecticide DDT mixture of Example 26 to yield 9 parts of encapsulated product containing 16.7% chlorine and 33.4% core material.

EXAMPLE 28

The encapsulation process described in Example 3 was repeated with 42.5 parts of starch xanthate solution of Example 1(c), 3 parts NaNO$_2$, and 4 parts of the insecticide DDT mixture of Example 26 to yield 10.4 parts of encapsulated product containing 19.7% chlorine and 39.4% core material.

EXAMPLE 29

The encapsulation process described in Example 3 was repeated with 44 parts of starch xanthate solution of Example 1(a), 1 part NaNO$_2$, and 1 part of the insecticide 2,3-dihydro-2,2-dimethyl-7-benzofuranyl methyl carbamate in 9 parts acetone to yield 7 parts of encapsulated product containing 0.88% nitrogen and 12.8% core material.

EXAMPLE 30

The encapsulation process described in Example 3 was repeated with 23.5 parts of starch xanthate solution of Example 1(d), 1 part NaNO$_2$, and 2.5 parts of the herbicide S-ethyl diisobutylthiocarbamate to yield 6.7 parts of encapsulated product containing 2.0% nitrogen and 31% core material.

EXAMPLE 31

The encapsulation process described in Example 3 was repeated with 33 parts of starch xanthate solution of Example 1(a), 0.8 part NaNO$_2$, and 4 parts methyl 4-allyl-2-methoxyphenol male insect sex lure to yield 7.8 parts of encapsulated product containing 41.7% core material based on weight increase.

A sample of encapsulated product was suspended in water in a test tube fitted with a stopper for 15 minutes. A strong odor was detected characteristic of the core material upon removing the stopper. No odor could be detected from dry product.

EXAMPLE 32

The encapsulation process described in Example 7 was repeated with 21 parts of starch xanthate solution of Example 1(a), 2 parts glacial acetic acid, 2 parts ammonium sulfate dissolved in 3 parts water, and 1 part 20% aqueous H$_2$O$_2$. The insolubilized material was filtered, washed with acetone, and dried at 25° C. to yield 5.7 parts of encapsulated product containing 4.4% nitrogen and 20.6% core material. This product is useful as a slow release fertilizer.

EXAMPLE 33

The encapsulation process described in Example 7 was repeated with 20.7 parts of starch xanthate solution of Example 1(a), 1 part glacial acetic acid, 2 parts urea, and 1 part 20% aqueous H$_2$O$_2$. The insolubilized material was filtered, washed with acetone, and dried at 25° C. to yield 3.8 parts of encapsulated product containing 6.3% nitrogen and 13.5% core material. The product is useful as a slow release fertilizer.

EXAMPLE 34

A commercial anionic phosphated starch was treated in the manner described in Example 1 to provide an anionic starch xanthate D.S. 0.35 in a 13.4% aqueous solution.

Forty parts of the anionic starch xanthate solution were mixed with 0.9 part NaNO$_2$ and 8 parts of the insecticide DDT in 15 parts acetone. The mixture was acidified with 5 parts glacial acetic acid, and the resulting insolubilized material was washed with water, filtered, washed with 200 parts hexane, and dried at about 25° C. to yield 11.8 parts of encapsulated product containing 25.8% chlorine and 51.6% core material.

EXAMPLE 35

A commercial cationic aminated starch was treated in the manner described in Example 1 to provide a cationic starch xanthate D.S. 0.35 in a 13.4% aqueous solution.

Forty-two parts of cationic starch xanthate were mixed with 5 parts of the sex lure tertiarybutyl 4-chloro-2-methyl cyclohexane carboxylate, 2 parts glacial acetic acid, and 2 parts 20% aqueous H$_2$O$_2$. The resulting insolubilized material was washed with water, filtered, and dried at about 25° C. to yield 9.8 parts of encapsulated product containing 41.8% core material (by weight increase).

EXAMPLE 36

The encapsulation process described in Example 7 was repeated with 20.3 parts of the starch xanthate solution of Example 1(a), 5 parts of 25% aqueous acetic acid, 0.5 part of 20% aqueous H$_2$O$_2$, and 3.1 parts of the herbicide S-ethyl diisobutylthiocarbamate for the first encapsulation, and 4.2 parts of starch xanthate solution of Example 1(a), 0.25 part of 20% aqueous H$_2$O$_2$, and 2 parts of 25% aqueous acetic acid to yield 5.2 parts of a double encapsulated product containing 2.6% nitrogen and 40% core material.

Four containers were filled with a mixture of 50 g. of top soil and 13 mg. of the above encapsulated product and four containers were filled with 50 g. of top soil only. One hundred grass seeds were distributed on the soil surface in each of the eight containers, and the container was watered every 48 hours with 20 ml. of water. After 1 week the grass in the containers with top soil alone exhibited from 60–100% grass seed germination, while in the containers with the encapsulated product there was no germination observed.

EXAMPLE 37

Germination studies of Example 36 were repeated with a mixture of top soil and the encapsulated product of Example 3. No germination was observed after 10 days.

EXAMPLE 38

Ninety-nine parts of starch xanthate solution of Example 1(a) were mixed with 8.6 parts of S-ethyl diisobutylthiocarbamate followed by 2.1 parts of epichlorohydrin, 0.58 part of sodium nitrite and 7 parts of glacial acetic acid. After standing for 10 minutes, the encapsulated product was washed with water, filtered, and dried to yield 19 parts containing 21% core material. Nine containers each were filled with 30 g. of moist top soil. On top of each of three of them, 13 mg. of the above encapsulated product was added; to another three, 13 mg. of the encapsulated product was incorporated in the soil, and the rest were kept as standards (no additives). One hundred grass seeds were dispersed on top of each container. Water was added as needed to keep the soil moist. After 10 days germination and growth in the first and second set were about 90% less than for the standards.

EXAMPLE 39

Sixty-nine parts of starch xanthate solution of Example 1(a) were mixed with 4 parts of S-ethyl diisobutylthiocarbamate followed by 4 parts of glacial acetic acid and 3 parts of epichlorohydrin to give on standing a rubbery product which on drying yielded 16.5 parts containing 0.9% nitrogen and 13.6% core material.

EXAMPLE 40

Thirty-six parts of starch xanthate solution of Example 1(a) were mixed with 2 parts of polystyrene contained in 10 parts of benzene and 6 parts of 1,2-dibromo-3-chloropropane, followed by 3 parts of glacial acetic and 2 parts of hydrogen peroxide (20%). The product was washed, filtered, and dried to yield 15.8 parts containing 31.5% core material.

EXAMPLE 41

Forty-two parts of starch xanthate solution of Example 1(a) were mixed with 1 part of polystyrene contained in 5 parts of benzene and 4 parts of 1,2-dibromo-3-chloropropane followed by 3 parts of glacial acetic and 2 parts of hydrogen peroxide (20%). The product was washed, filtered, and dried to yield 10.75 parts containing 25.4% core material.

One thousand and forty-six milligrams of the encapsulated product were covered with water for 3 days then dried to yield 23% core material.

EXAMPLE 42

Forty-five parts of starch xanthate solution of Example 1(a) were mixed with 5 parts of polystyrene contained in 10 parts of benzene along with 6 parts of 1,2-dibromo-3-chloropropane followed by 3 parts of glacial acetic acid and 2 parts of hydrogen peroxide (30%). The encapsulated product was washed and dried to yield 17 parts containing 26.6% core material. A sample of this product was immersed in water and after 1 day an aliquot was dried and analyzed to yield 23.6% core material. After 6 days another aliquot was dried and analyzed to yield 21.5% core material.

EXAMPLE 43

Sixty-seven parts of starch xanthate solution of Example 1(a) were mixed with 7 parts of 1,2-dibromo-3-chloropropane, followed by the addition of 8 parts of glacial acetic acid and 4 parts of 30% hydrogen peroxide for the first encapsulation. The granular particles thus formed were mixed with 18 parts of starch xanthate solution of Example 1(a) and 1.5 parts of polystyrene in 7.5 parts benzene, followed by addition of 2 parts of glacial acetic acid and 1 part of 30% hydrogen peroxide to yield after drying 28 parts of a double encapsulated product containing 28% active ingredient.

EXAMPLE 44

One hundred and seventy-one parts of starch xanthate solution of Example 1(a) were mixed with 17 parts of latex SBR 1502 (20% solids) along with 17 parts of emulsifiable concentrate containing 7.25% core material of 1,2-dibromo-3-chloropropane. Crosslinking of the xanthate was done by adjusting the pH of the mixture with 9 parts of glacial acetic acid followed by the addition of 5 parts of 30% hydrogen peroxide. The encapsulated product was mixed in a Waring blendor with silica (2% on a dry weight basis) to give fine particles containing 5.6% core material.

EXAMPLE 45

Sixty-seven parts of starch xanthate solution of Example 1(a) were mixed with 7 parts of 1,2-dibromo-3-chloropropane, followed by the addition of 8 parts of glacial acetic acid and 4 parts of 30% hydrogen peroxide for the first encapsulation. The granular particles thus formed were washed with water, filtered, then mixed with 10 parts of latex SBR 1502, 1 part of glacial acetic acid, followed by drying to yield 17 parts of a double encapsulated product containing 27% active ingredient.

EXAMPLE 46

Seventy-four parts of starch xanthate solution of Example 1(a) were mixed with 15 parts latex SBR 1502 containing 20% solids and 10 parts of 1,2-dibromo-3-chloropropane followed by 2 parts of glacial acetic acid and 3 parts of 30% hydrogen peroxide. The solid particles thus obtained were diluted with 100 parts of water and mixed in a Waring blendor for 6 minutes followed by filtration and drying at 25° to yield 18 g. product containing 27.5% core material.

A sample of 2 g. of the encapsulated product was coated with 3 ml. benzene containing 200 mg. polystyrene. The dried product weighed 2.2 g. and contained 26.4% core material. Water treatment of 200-mg. sample for 20 hours yielded after drying 188 mg. of product containing 22% core material. Water treatment of another 200-mg. sample for 8 days yielded after drying 162 mg. of product containing 8.8% core material.

EXAMPLE 47

Fifty-two parts of starch xanthate solution of Example 1(a) were mixed with 5 parts of latex SBR 1502, 1 part of polystyrene in 5 parts of benzene, and 7 parts of 1,2-dibromo-3-chloropropane, followed by the addition of 6 parts of glacial acetic acid and 3 parts of 30% hydrogen peroxide. The granular particles thus formed were washed, filtered, and dried to yield 16 parts of encapsulated product containing 33% active ingredient.

EXAMPLE 48

Eighty-two parts of starch xanthate solution of Example 1(a) were mixed with 8 parts of latex SBR 1502 (containing 20% solids) along with 5 parts of S-ethyl diisobutylthiocarbamate, 2 parts of glacial acetic acid, and 2.9 parts of epichlorohydrin. On mixing for a few minutes the product solidified. After water washing and drying the yield was 21 parts of yellow particles containing 1.1% nitrogen and 17% core material.

EXAMPLE 49

One hundred and sixty-one parts of starch xanthate solution of Example 1(a) were mixed with 16 parts of latex SBR 1502 (20%) solids) along with 9 parts of herbicide S-ethyl diisobutylthiocarbamate and 9 parts of nematocide 1,2-dibromo-3-chloropropane. The mixture was acidified with 8 parts of glacial acetic acid followed by addition of 5 parts of 30% hydrogen peroxide solution, 2 parts of 58% sodium nitrite, and 3 parts of glacial acetic acid. The encapsulated herbicide-nematocide was washed with water, filtered, and dried to yield 41 parts containing 10.5% halogen and 12.7% nematocide, 1.32% nitrogen and 20% herbicide.

EXAMPLE 50

Eighty-seven parts of starch xanthate solution of Example 1(a) were mixed with 7 parts of melted α,α,α-trifluoro-2,6-dinitro-N,N-dipropyl-p-toluidine (m.p. 49° C.) along with 12 parts of latex SBR 1502 (20% solids) and 2 parts of epichlorohydrin, followed by 0.58 part of sodium nitrite and 7 parts of glacial acetic acid. After standing at ambient temperature for a few minutes, the product was washed, filtered, and dried to yield 23 parts of encapsulated material containing 30% of core material.

EXAMPLE 51

One hundred and fifteen parts of starch xanthate solution of Example 1(a) were mixed with 15 parts of latex SBR 1502 (20% solids) and 8.6 parts of S-ethyl diisobutylthiocarbamate along with 2.6 parts of epichlorohydrin, 0.9 part of sodium nitrite, and 10 parts of glacial acetic acid. After standing at 25° C. for 10 minutes with occasional stirring, the second encapsulation was performed by mixing the product with 40 parts of starch xanthate solution of Example 1(a), followed by 0.7 part of epichlorohydrin, 0.3 part of sodium nitrite, and 3 parts of glacial acetic acid. The new product was washed, filtered, and dried to yield 36 parts containing 19.6% parts of core material. One gram of the double encapsulated product lost no core material through evaporation by standing for 20 hours at 25° C. in an open container; while under same conditions free core material completely evaporated.

EXAMPLE 52

Seventy-four parts of starch xanthate solution of Example 1(a) were heated to 50° C. and mixed with 2 parts of melted tallow alcohol, 10 parts of 1,2-dibromo-3-chloropropane, 5 parts of glacial acetic acid, and 5 parts of 20% hydrogen peroxide to yield 18.5 parts of encapsulated product containing 33.6% core material.

A sample of 305 mg. after being immersed in water for 3 days was dried to give a product containing 23.8% core material.

EXAMPLE 53

Fifty-two parts of starch xanthate solution of Example 1(a) were heated to 50° C. and mixed with 2 parts of melted tallow alcohol followed by 8.3 parts of S-ethyl diisobutylthiocarbamate, 3 parts of glacial acetic, and 3 parts of 20% hydrogen peroxide to yield 17.5 parts of encapsulated product containing 47.5% core material (i.e., 3.1% nitrogen).

EXAMPLE 54

Eighty-three parts of starch xanthate solution of Example 1(a) were mixed with 9 parts of 85% nemacure in 10 parts acetone along with 12 parts latex SBR 1502 (20% solids), 2.6 parts sodium nitrite, 0.7 part resorcinol, 0.7 part of 37% formaldehyde followed by the addition of 12 parts glacial acetic acid. After continuation of mixing for 5 minutes, the resulting insolubilized material was filtered, washed with water, and dried at about 25° C. to yield 23.5 parts of encapsulated product containing 32.5% core material.

EXAMPLE 55

One hundred and twenty-five parts of starch xanthate solution of Example 1(a) were mixed in a Waring blendor with air-milled herbicide N-(5-1,1-dimethylethyl)-1,3,4-thiadiazol-2-yl)-N,N'-dimethylurea along with 6 parts of glacial acetic acid and 3 parts of 30% hydrogen peroxide solution to give a solid mass which was then treated with 0.5 part of sodium nitrite, 1 part of 50% resorcinol solution, and 1 part of 37% formaldehyde. Addition of the last three ingredients made the particles heavier and thus much easier to filter. The encapsulated product was dried at 85° C. for 10 minutes followed by room temperature drying for 18 hours to yield 61 parts of encapsulated material containing 60% active ingredient (based on increase of weight). Upon immersing dry sample in an aqueous iodine solution, the sample turned dark blue because of iodine uptake by the starch which is surrounding the core material. No change in color of the technical core material occurred upon mixing with iodine solution.

EXAMPLE 56

One hundred forty parts of starch xanthate solution of Example 1(a) were heated to 35° C. and mixed with melted 16.3 parts of Thiofenox followed by the addition of 5 parts of glacial acetic acid and 5 parts of hydrogen peroxide (30%). Within 5 minutes of mixing, the mixture solidified which in turn entrapped the core material. A second layer of encapsulation was provided by mixing the product in a Waring blendor with 34 parts of the xanthate solution of Example 1(a) along with 1.7 parts of sodium nitrite, 1 part resorcinol aqueous solution (50% concentration), 1 part of 37% formaldehyde, and 3 parts of glacial acetic acid. The product turned again to a solid mass which was washed with water and dried at 25° to yield 47 parts containing 4.4% nitrogen and 32% core material.

EXAMPLE 57

One hundred and nineteen parts of starch xanthate solution of Example 1(a) were mixed with 12 parts of latex SBR 1502 (20% solids), 15 parts of herbicide 3-[2-(3,5-dimethyl-2-oxocyclohexyl)-2-hydroxyethyl]-glutarimide dissolved in 16 parts of warm acetone followed by the addition of 6 parts of glacial acetic acid and 3.5 parts of 30% hydrogen peroxide solution. The encapsulated herbicide was mixed with 39 parts of starch xanthate solution of Example 1(a) along with 9 parts of 1,2-dibromo-3-chloropropane followed by treatment with 2 parts of 58% solution of sodium nitrite, 1 part of 50% solution of resorcinol, 1 part of 37% of formaldehyde, and 2 parts of glacial acetic acid. The product containing encapsulated herbicide and encapsulated nematocide was washed with water, filtered, and dried to yield 41.5 parts containing 6.7% halogen and 8.1% nematocide, 1.55% nitrogen, and 31% herbicide.

EXAMPLE 58

One hundred and thirty parts of starch xanthate solution of Example 1(a) were mixed with 4.5 parts of O-ethyl-S-phenylethyl phosphorodithioate and 10 parts of 15% polyethylene solution in warm toluene. The mixture was acidified with 6 parts of glacial acetic acid followed by the addition of 4 parts of 30% hydrogen peroxide to yield encapsulated product which further was treated with 1 part of a 58% sodium nitrite, 1 part of 37% formaldehyde, and 1 part of 50% resorcinol solution. After mixing for 5 minutes, the product was washed with water, filtered, and dried to yield 28.5 parts containing 16% core material.

EXAMPLE 59

One hundred and fifty-three parts of starch xanthate solution of Example 1(a) were mixed with 6 parts of poly(vinyl chloride) (56% solids) along with 9.3 parts of O-ethyl-S-phenylethyl phosphorodithioate followed by 8 parts of glacial acetic acid and 5 parts of 30% hydrogen peroxide to yield encapsulated core material which was further treated with 1 part of sodium nitrite solution (58% solids), 1 part of 37% formaldehyde, and 1 part of 50% resorcinol. The final product was filtered, dried, and weighed to yield 38 parts containing 24.4% core material.

EXAMPLE 60

One hundred and fifty-six parts of starch xanthate solution of Example 1(a) were mixed with 12 parts of 10% solution of polymethyl methacrylate in methylene chloride followed by addition of 12 parts of chlordane. Crosslinking of the xanthate was accomplished by adjusting the pH to acidic by the addition of 8 parts of glacial acetic followed by addition of 5 parts of 30% hydrogen peroxide. After mixing for 2 minutes, 1 part of sodium nitrite solution (58% solids), 1 part of 37% formaldehyde, and 1 part of 50% resorcinol were added. The solid product was washed, filtered, and dried to yield 36 parts of product containing 33% core material.

EXAMPLE 61

Fifty-one parts of starch xanthate solution of Example 1(a) were mixed with 10 parts of latex SBR 1502 along with 4.7 parts of S-ethyl dipropylthiocarbamate. Latex curing accelerator reagents were added (consisting of 0.1 part of sulfur in 1 part of carbon disulfide and 0.2 part of butyl 8). Oxidation of the xanthate was achieved by addition of 3 parts of glacial acetic acid followed by 2 parts of 20% hydrogen peroxide. The encapsulated core material was doubly encapsulated by addition of 42 parts of starch xanthate solution of Example 1(a), mixing thoroughly, and adding 3 parts of glacial acetic acid followed by 2 parts of hydrogen peroxide (20%). The final product was washed with water, filtered, and dried to yield 20.5 parts containing 22% parts core material.

EXAMPLE 62

Ninety-four parts of starch xanthate solution of Example 1(a) were mixed with 10 parts of neoprene latex containing 46% solids along with 9 parts of S-propyl dipropylthiocarbamate. The mixture was divided into 2 parts, to one of which latex curing accelerator reagents (consisting of 0.3 part of butyl 8, 0.07 part of elemental sulfur in 0.3 part of carbon disulfide) were added. To each part, 0.5 part of resorcinol solution (50% in water), 0.5 part of 37% solution of formaldehyde, and 0.5 part of 58% sodium nitrite solution was added. Each part was then mixed and acidified with 2 parts of glacial acetic acid, to give a solid product which was washed with water, filtered, and dried to yield 13.5 parts (each half) containing 32% core material.

A sample of the product treated with accelerator and a sample of the untreated were immersed separately in water. The water was exchanged periodically and after 48 hours the products were filtered and dried. Analyses revelated loss of 10% of core material in the curing accelerator-treated product versus loss of 16% in the untreated product.

EXAMPLE 63

Eighteen parts of acid modified corn flour xanthate from Example 1(e) were mixed with 9 parts of 1,2-dibromo-3-chloropropane followed by 4 parts of glacial acetic acid and 2.5 parts of 30% hydrogen peroxide. The insolubilized mixture was mixed with an additional 6.5 parts modified corn flour xanthate from Example 1(e) followed by 0.5 part of 58% sodium nitrite solution and 1.5 parts of glacial acetic acid. The crumbly mass thus obtained was pulverized in a Waring blendor and dried to yield 37 parts of a yellowish powder containing 20% active ingredient.

EXAMPLE 64

Seventy parts of acid modified starch xanthate from Example 1(f) were mixed with 20 parts of latex SBR 1502 (20% solids) and 15.5 parts of the insecticide 3,3-dimethyl-1-(methylthio)-2-butanone O-[(methylamino)-carbonyl]oxime followed by 9 parts of glacial acetic acid and 4.5 parts of 30% hydrogen peroxide to yield a crumbly mass. The mass was then coated with 14 parts of the acid modified starch xanthate from Example 1(f) followed by 0.5 part of 58% sodium nitrite solution and 3 parts of glacial acetic acid. The product was ground in a Waring blender and dried to yield 68 parts of encapsulated product containing 22% active ingredient. The product was then coated with 4 parts of polystyrene dissolved in 20 parts benzene and dried.

We claim:

1. A method of encapsulating a chemical biological agent comprising the steps of:
    a. preparing a dispersion or solution of a suitable chemical biological agent in a first matrix-forming material comprising an aqueous solution of a polyhydroxy polymer xanthate (PPX) having a xanthate degree of substitution (D.S.) of from about 0.1 to 3, wherein said solution has a concentration of PPX of from about 5–70%, and wherein the relative amount of said PPX with respect to said biological agent is sufficient to entrap said agent within a matrix of said PPX;
    b. reacting from a single phase said PPX with a coupling agent selected from the group consisting of sodium nitrite, nitrous acid, iodine, chlorine, sodium tetrathionate, cyanogen bromide, nitrosyl chloride, chloramine T, hydrogen peroxides, and water-soluble salts of polyvalent metal ions at a pH of from about 2 to about 7 to form a first insolubilized matrix thereby entrapping said agent; and
    c. recovering said entrapped chemical biological agent.

2. A method as described in claim 1 wherein the suitable chemical biological agent is a herbicide, insecticide, fungicide, nematocide, bacteriocide, rodenticide, moluscide, acaricide, larvacide, fumigant, animal repallent, insect repellent, bird repellent, plant growth regulator, fertilizer, pheromone, sex lure, flavor composition, or odor composition.

3. A method as described in claim 1 wherein the suitable chemical biological agent is S-propyl dipropylthiocarbamate, $\alpha,\alpha,\alpha$-trifluoro-2,6-dinitro-N,N-dipropyl-p-toluidine, S-ethyl diisobutylthiocarbamate, 2,6-dichlorobenzonitrile, 1,1'-dimethyl-4,4'-bipyridinium dichloride, 2,4-dichlorophenoxy acetic acid, sodium 2,4-dichlorophenoxy acetate, ammonium 3-amino-2,5-dichlorobenzoate, 1,2-dibromo-3-chloropropane, O-ethyl-S-phenylethyl phosphorodithioate, S-(1,2-dicarbethoxyethyl)-O,O-dimethyl dithiophosphate, methyl O,O-diethyl-o,p-nitrophenyl phosphorothioate, 1,1,1-trichloro-2,2-bis(p-chlorophenyl)ethane, 2,3-dihydro-2,2-dimethyl-7-benzofuranyl methyl carbamate, methyl 4-allyl-2-methoxyphenol, or tertiarybutyl 4-chloro-2-methyl cyclohexane carboxylate.

4. A method as described in claim 1 wherein the PPX is a xanthate of starch, starch fractions, methyl starch, hydroxyethyl starch, cereal flours, depolymerized flours, cellulose, methyl cellulose, hydroxyethyl cellulose, dextran, dextrin, guar gum, biopolymer gums, cationic starch, anionic starch, or synthetic polyalcohols.

5. A method as described in claim 1 wherein the PPX is a xanthate of starch, cellulose, cationic starch, or anionic starch.

6. A method as described in claim 1 wherein the suitable chemical biological agent in step (a) is present in amounts equal to from about 1% to about 100% of the total amount of the matrix-forming material on a dry weight basis.

7. A method as described in claim 1 wherein the coupling agent is selected from the group consisting of sodium nitrite, nitrous acid, iodine, chlorine, sodium tetrathionate, cyanogen bromide, nitrosyl chloride, chloramine T, and hydrogen peroxide.

8. A method as described in claim 1 wherein the coupling agent is a water-soluble salt of $Zn^{+2}$, $Fe^{+3}$, or $Cu^{+2}$.

9. A method as described in claim 1 and further comprising hardening said matrix by adding an effective amount of a hardening agent comprising a combination of resorcinol and formaldehyde.

10. A method as described in claim 1 wherein said matrix-forming material further comprises a synthetic polymer selected from the group consisting of polyvinyl and polyacrylic polymers in an amount of up to 30% based on the total dry weight of said matrix-forming material.

11. A method as described in claim 1 wherein said matrix-forming material further comprises a rubber latex in amounts such that the ratio of rubber latex:PPX is from about 4:1 to about 1:9 by dry weight.

12. A method as described in claim 11 wherein said rubber latex is selected from the group consisting of styrene-butadiene, styrene-acrylonitrile-butadiene, acrylonitrile-butadiene, isoprene, isoprene-acrylonitrile, isoprene-butadiene, and chloroprene.

13. A method as described in claim 11 wherein said matrix-forming material further comprises a rubber curing agent.

14. A method as described in claim 1 and further comprising the following steps:
b'. redispersing said first matrix from step (b) in a second matrix-forming material comprising an aqueous solution of PPX having a xanthate D.S. of from 0.1 to 3;
b''. reacting from a single phase said PPX in step (b') with a coupling agent selected from the group consisting of sodium nitrite, nitrous acid, iodine, chlorine, sodium tetrathionate, cyanogen bromide, nitrosyl chloride, chloramine T, hydrogen peroxides, and water-soluble salts of polyvalent metal ions at a pH of from about 2 to about 7 to form a second insolubilized matrix, thereby further entrapping said chemical biological agent.

15. A method as described in claim 14 wherein the coupling agent in step (b'') is selected from the group consisting of sodium nitrite, nitrous acid, iodine, chlorine, sodium tetrathionate, cyanogen bromide, nitrosyl chloride, chloramine T, and hydrogen peroxide.

16. A method as described in claim 14 wherein the coupling agent in step (b'') is a water-soluble salt of $Zn^{+2}$, $Fe^{+3}$, or $Cu^{+2}$.

17. A method as described in claim 14 and further comprising hardening said first and second matrices by adding an effective amount of a hardening agent comprising a combination of resorcinol and formaldehyde.

18. A method as described in claim 14 wherein said second matrix-forming material further comprises a synthetic polymer selected from the group consisting of polyvinyl polymers and polyacrylic polymers in an amount of up to 30%, based on the total dry weight of said second matrix-forming material.

19. A method as described in claim 14 wherein said second matrix-forming material further comprises a rubber latex in amounts such that the ratio of rubber latex:PPX is from about 4:1 to about 1:9 by dry weight.

20. A method as described in claim 19 wherein said rubber latex is selected from the group consisting of styrene-butadiene, styrene-acrylonitrile-butadiene, acrylonitrile-butadiene, isoprene, isoprene-acrylonitrile, isoprene-butadiene, and chloroprene.

21. A method as described in claim 19 wherein said second matrix-forming material further comprises a rubber curing agent.

22. A method as described in claim 1 and further comprising the following steps:
d. dispersing the entrapped agent from step (c) in a solution of a synthetic polymer dissolved in a suitable organic solvent, said polymer selected from the group consisting of polyvinyl polymers and polyacrylic polymers, thereby coating said entrapped agent with said polymer; and
e. recovering said coated entrapped chemical biological agent.

23. A composition of matter produced by the process of claim 1.

24. A composition of matter produced by the process of claim 2.

25. A composition of matter produced by the process of claim 3.

26. A composition of matter produced by the process of claim 4.

27. A composition of matter produced by the process of claim 5.

28. A composition of matter produced by the process of claim 9.

29. A composition of matter produced by the process of claim 10.

30. A composition of matter produced by the process of claim 11.

* * * * *